United States Patent [19]

Yamamoto et al.

[11] 4,256,672
[45] Mar. 17, 1981

[54] PROCESS FOR THE PREPARATION OF PHOSPHORIC ESTERS AND THIOPHOSPHORIC ESTERS

[75] Inventors: Ryuichi Yamamoto; Masaaki Torisu, both of Omuta, Japan

[73] Assignee: Mitsui Toatsu Chemicals, Inc., Tokyo, Japan

[21] Appl. No.: 88,021

[22] Filed: Oct. 25, 1979

[51] Int. Cl.³ ............................ C07F 9/09; C07F 9/165
[52] U.S. Cl. ..................................... 260/974; 260/944
[58] Field of Search ........................................ 260/974

[56] References Cited

U.S. PATENT DOCUMENTS 1,837,176  12/1931  ter Horst .............................. 260/974

Primary Examiner—Anton H. Sutto
Attorney, Agent, or Firm—Fisher, Christen & Sabol

[57] ABSTRACT

Disclosed is a process for the preparation of an ester compound selected from phosphoric esters and thiophosphoric esters which comprises reacting a hydroxyl-containing organic compound with phosphorus oxychloride or phosphorus thiochloride in the presence of the hydroxide or carbonate of an alkali metal, water, and an organic solvent.

10 Claims, No Drawings

PROCESS FOR THE PREPARATION OF PHOSPHORIC ESTERS AND THIOPHOSPHORIC ESTERS

BACKGROUND OF THE INVENTION (a) Field of the Invention

This invention relates to a new and improved process for the preparation of phosphoric esters and thiophosphoric esters by reaction of a hydroxyl-containing organic compound with phosphorus oxychloride or phosphorus thiochloride.

(b) Description of the Prior Art

Phosphoric esters and thiophosphoric esters which are reaction products of alcohols or phenols with phosphorus oxychloride or phosphorus thiochloride have long been produced for use as agricultural chemicals, resin additives (flameretardant plasticizers), and the like or in the manufacture thereof. For example, tricresyl phosphate (hereinafter referred to as TCP) which is a reaction product of cresol with phosphorus oxychloride was initially developed as a plasticizer for cellulose nitrate and subsequently came into wide use as a plasticizer for polyvinyl chloride. Thus, a variety of processes for the preparation thereof have been proposed in the past.

The preparation of TCP is discussed from the viewpoint of reaction kinetics, for example, in "Kagaku-to-Kogyo," Vol. 4, No. 12, pp. 7-12. It is described therein that the processes for the preparation of TCP which have heretofore been reported in the literature can be classified into four categories:

(a) non-catalytic method, (b) basic catalyst method, (c) acid catalyst method, and (d) metallic salt method.

(a) In the non-catalytic method, the esterification reaction of phosphorus oxychloride is retarded as more chlorine atoms of the phosphorus oxychloride are replaced by phenyl radicals. Moreover, the frequency factor is also reduced so that the rate of formation of substituted products is decreased. Accordingly, high temperatures and long times are required for the completion of the reaction.

(b) The basic catalyst method generally involves the use of tertiary amines. In this case, the rate of formation of mono- and diesters is enhanced. However, such basic catalysts are not effective in promoting the formation of triesters.

(c) The acid catalyst method is based on the use of anhydrous aluminum chloride, iron chloride, magnesium chloride, and the like. For example, when aluminum chloride is used, the rate of formation of di- and triesters is not decreased and, therefore, the reaction can be completed at a relatively low temperature in a short period of time. However, the use of aluminum chloride necessarily induces a Friedel-Crafts reaction which gives rise to undesired compounds having one or more phenyl radicals attached directly to the phosphorus atom.

(d) The metallic salt method is the most typical one that is used in the field of organic synthesis. According to this method, the reaction can be completed at a low temperature in a short period of time, and the product can be obtained in quantitative yield. However, it is described in the literature that this method is not suitable for industrial purposes, in view of its economic disadvantages such as the necessity of converting cresol into a metallic salt.

SUMMARY OF THE INVENTION

It is an object of the present invention to provide a process for the preparation of a phosphoric ester or thiophosphoric ester in which the ester can be prepared in good yield and with ease from a hydroxyl-containing organic compound and phosphorus oxychloride or phosphorus thiochloride.

It is another object of the present invention to provide a process for the preparation of a phosphoric ester or thiophosphoric ester by use of an organic compound containing a hydroxyl group and one or more other groups capable of reacting with phosphorus oxychloride or phosphorus thiochloride in which only the hydroxyl group of the organic compound is allowed to react selectively with phosphorus oxychloride or phosphorus thiochloride.

These objects are accomplished by a process for the preparation of an ester compound selected from the group consisting of phosphoric esters and thiophosphoric esters by reaction of a hydroxyl-containing organic compound with phosphorus oxychloride or phosphorus thiochloride wherein the improvement comprises carrying out the reaction in the presence of (a) at least one alkali metal compound selected from the group consisting of the hydroxides and carbonates of alkali metals, (b) water, and (c) an organic solvent.

Preferably, the aforesaid hydroxyl-containing organic compound is selected from the group consisting of compounds of the formula

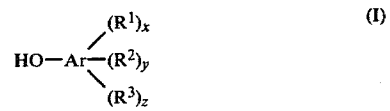

where $R^1$ is a hydrogen atom, alkyl radical, alkenyl radical, alkoxy radical, alkoxyalkyl radical, aryl radical, aralkyl radical, aryloxy radical, or arylsulfonyl radical and the organic radicals represented by $R^1$ may further contain one or more halogen, lower alkyl, or lower alkoxy substituents, $R^2$ is a hydrogen atom, nitro group, nitroso group, amino group, mono- or dialkylamino group, or mono- or diacylamino group, $R^3$ is a hydrogen atom or halogen atom, Ar is an aromatic radical, and x, y, and z are whole numbers ranging from 0 to 5 and the sum $(x+y+z)$ is equal to or less than 5, and compounds of the formula

where R is an alkyl radical, alkenyl radical, alkoxyalkyl radical, cycloalkyl radical, or aralkyl radical and the radicals represented by R may further contain one or more lower alkyl, lower alkoxy, lower alkoxyalkyl, or halogen subtituents.

DETAILED DESCRIPTION OF THE INVENTION

The present inventors have found that phosphoric esters and thiophosphoric esters can be obtained in good yield by reacting a hydroxyl-containing organic compound with phosphorus oxychloride or phosphorus thiochloride at a relatively low temperature in the presence of the hydroxide or carbonate of an alkali metal, water, and an organic solvent. In the past, phosphorus oxychloride and phosphorus thiochloride have been believed to undergo hydrolysis on contact with water. It is surprising, therefore, that phosphorus oxychloride or phosphorus thiochloride reacts with a hydroxyl-containing organic compound in the presence of an alkali and water to give a phosphoric ester or thiophosphoric ester in good yield. This is presumably because, in the presence of an alkali and water, the reaction of the hydroxyl group with phosphorus oxychloride or phosphorus thiochloride proceeds more rapidly than the hydrolysis of phosphorus oxychloride or phosphorus thiochloride.

The reaction of a hydroxyl-containing organic compound with phosphorus oxychloride or phosphorus thiochloride may be carried out in any of several manners. In accordance with one preferred embodiment, phosphorus oxychloride or phosphorus thiochloride is added to a hydroxyl-containing organic compound in the presence of an organic solvent and, while the resulting mixture is kept at a temperature of 80° C. or below, an aqueous solution or suspension of the hydroxide or carbonate of an alkali metal is added thereto drop by drop. In accordance with another preferred embodiment, the hydroxide or carbonate of an alkali metal and water are added to a hydroxyl-containing organic compound and, while the resulting mixture is cooled, phosphorus oxychloride or phosphorus thiochloride is added thereto drop by drop.

As described above, the hydroxyl-containing organic compound is preferably selected from the group consisting of compounds of formulas (I) and (II). The compounds which are within the scope of formula (I) include, for example, phenol; mono-, di-, tri-, tetra-, and pentaalkylphenols; mono-, di-, and trialkoxyphenols; alkyl-alkoxyphenols; mono- and dialkenylphenols; alkenylalkoxyphenols; mono-, di-, tri-, tetra-, and pentahalophenols; alkyl-halophenols, alkoxy-halophenols, and nitro-halophenols; mono-, di-, and trinitrophenols; alkyl-nitrophenols and alkoxynitrophenols; aminophenols; N-monoalkylaminophenols and N,N-dialkylaminophenols; N-monoacylaminophenols and N,N-diacylaminophenols; amino-alkylphenols, amino-nitrophenols, and aminohalophenols; phenylphenols; phenylalkylphenols; cyclohexylphenols; cyclohexylalkylphenols; phenoxyphenols; phenylsulfonylphenols; cyclohexyloxyphenols; and various isomers of the foregoing compounds as well as the compounds obtained by substituting the naphthalene nucleus for the benzene nucleus in the foregoing compounds. The compounds which are within the scope of formula (II) include, for example, alkanols, alkenols, cyclohexanol, alkylcyclohexanols, alkoxyalkanols, phenylalkanols, alkylphenylalkanols, halophenylalkanols, haloalkanols, and various isomers of the foregoing compounds. These compounds may be used alone or as mixtures of up to 3 ingredients.

The hydroxyl-containing organic compound and the phosphorus oxychloride or phosphorus thiochloride are used in a molar ratio ranging from 2.5:1 to 20:1. Generally, the phosphorus oxychloride or phosphorus thiochloride which undergoes some degree of hydrolysis during the reaction may as well be used slightly in excess of the stoichiometric amount to enhance the yield based on the amount of the hydroxyl-containing organic compound. However, if it is too much, mono- and diesters are formed as by-products. If the amount of phosphorus oxychloride or phosphorus thiochloride used is less than the stoichiometric amount, some of the hydroxyl-containing organic compound remains unreacted and, therefore, an additional step is required for the recovery thereof. The preferred range of the molar ratio is from 2.5:1 to 3.5:1.

The alkali metal compound (hereinafter referred to as the alkali) is typically selected from the hydroxides and carbonates of sodium and potassium and suitably used in the form of an aqueous solution or suspension (hereinafter referred to as an alkaline water) containing the alkali at a concentration of from 20 to 60% by weight.

Preferably, the alkali is used in an amount equal to or slightly in excess of the stoichiometric amount, i.e. 3 moles per mole of the phosphorus oxychloride or phosphorus thiochloride.

As described above, the concentration of the alkali in the alkaline water is suitably from 20 to 60% by weight. If the concentration is lower than 20% by weight, the remaining chlorine atoms of the phosphorus oxychloride or phosphorus thiochloride and the resulting intermediate products (mono- and diesters) are apt to undergo hydrolysis. If it is higher than 60% by weight, the rate of reaction is undesirably reduced to such an extent that the hydrolysis of phosphorus oxychloride or phosphorus thiochloride in the alkaline water tends to proceed more rapidly than the esterification reaction. The preferred range of the concentration is from 30 to 50% by weight.

The water is preferably added to the reaction system in the form of an alkaline water as defined above. Alternatively, the water alone may be added to the system, followed by the addition of the alkali thereto. In this case, the amount of water added should be such that the alkaline water to be formed in the reaction system contains the alkali at a concentration of from 20 to 60% by weight.

The organic solvent may be any of the organic solvents which have inertness to phosphorus oxychloride or phosphorus thiochloride and can dissolve the hydroxyl-containing organic compound used as a starting material. Specific examples of the organic solvent include ketones such as acetone, methyl ethyl ketone, methyl n-propyl ketone, methyl n-butyl ketone, methyl isobutyl ketone, diethyl ketone, etc.; ethers such as isopropyl ether, n-butyl ether, 1,4-dioxane, diethylene glycol, dimethyl ether, etc.; chlorinated aliphatic hydrocarbons such as chloroform, methylene chloride, ethylene dichloride, etc.; and unsubstituted or substituted aromatic hydrocarbons such as benzene, toluene, xylene, diethylbenzene, monochlorobenzene, dichlorobenzene, etc. If desired, the hydroxyl-containing organic compound may be used in excess so that it may also act as the solvent.

The reaction temperature is preferably 80° C. or below and more preferably from 0° to 50° C. If the reaction temperature is higher than this limit, the formation of by-products is undesirably increased as a result of the decomposition of the phosphorus oxychloride or phosphorus thiochloride. If it is too low, the rate of reaction is decreased and, therefore, the reaction time is prolonged so as to increase the formation of undesired hydrolyzates. The most preferred range of the reaction temperature is from 20° to 40° C.

The reaction time may vary according to the reaction temperature. Generally, the reaction time is suitably from 1 to 6 hours when the reaction temperature is within the above preferred range.

When a triester is prepared according to the present invention, the reaction mixture also contains small amounts of mono- and diesters, unreacted hydroxyl-containing organic compound, and hydrolyzates thereof. Accordingly, the reaction mixture is preferably treated as follows: The reaction mixture is first subjected to vacuum distillation so that the organic solvent and unreacted hydroxyl-containing organic solvent may be removed. Then, the concentrated reaction mixture is poured into water. The precipitate so formed is separated by filtration and then washed with an alkaline water to dissolve the by-products in the form of alkali metal salts. Thus, the desired triester can be isolated.

Where the product is in liquid form, the reaction mixture is washed with an alkaline water and then with water, and thereafter subjected to distillation.

According to the present invention, a phosphoric ester or thiophosphoric ester can be prepared in good yield from a hydroxyl-containing organic compound and phosphorus oxychloride or phosphorus thiochloride. Even if the hydroxyl-containing organic compound has one or more other functional groups capable of reacting phosphorus oxychloride or phosphorus thiochloride (as in p-aminophenol), only the hydroxyl group is allowed to react selectively with phosphorus oxychloride or phosphorus thiochloride whereby a desired product (for example, tris(4-aminophenyl)phosphate or tris(4-aminophenyl) thiophosphate) can be prepared directly.

In such a case, it has been regarded as quite impossible to effect the selective reaction of the hydroxyl group alone, because the amino group unavoidably reacts with phosphorus oxychloride or phosphorus thiochloride in prior art processes. Accordingly, several processes have been proposed for the purpose of preparing the aforesaid product. By way of example, one process is to synthesize a triphenyl ester (triphenyl phosphate or triphenyl thiophosphate), subject it to nitration, and then reduce the resulting nitro compound to the corresponding amine, and another is to react sodium p-nitrophenate with phosphorus oxychloride or phosphorus thiochloride and then reduce the resulting nitro compound to the corresponding amine. However, these processes involve the problem of safety because the nitro compound is highly explosive, and has the disadvantage of requiring laborious operations and great expenses. If the process of the present invention is employed in place of these complicated prior art processes, tris(4-aminophenyl) phosphate or tris(4-aminophenyl) thiophosphate can be prepared directly from p-aminophenol and phosphorus oxychloride or phosphorus thiochloride with great industrial advantages.

In addition, the process of the present invention is more advantageous than the metallic salt method, because the step of converting a hydroxyl-containing organic compound into a metallic salt can be eliminated and the reaction can readily be performed in a short period of time.

The present invention will be more fully understood by reference to the following examples. However, these examples are intended merely to illustrate the practice of the invention and are not to be construed to limit the scope of the invention.

EXAMPLE 1

Into a 3-liter four neck flask fitted with a stirrer, a thermometer, a condenser, and a dropping funnel were charged 2,000 ml of acetone and 139.1 g (1.0 mole) of p-nitrophenol. Then, 55.2 g (0.36 mole) of phosphorus oxychloride was added to the resulting solution. Immediately after that, 96.0 g (1.08 moles) of a 45%(w/w) aqueous solution of sodium hydroxide was added thereto dropwise, with vigorous stirring (at 600 rpm), through the dropping funnel over a period of 10 minutes. During this period, cooling with water was used to keep the reaction temperature at 30° C. or below. Thereafter, the reaction was further continued for 5 hours.

The reaction mixture was concentrated at 30°–40° C. under reduced pressure. Then, under cooling with ice, a 30%(w/w) aqueous soluion of sodium hydroxide was added dropwise to the reaction mixture until its pH reached 11. The resulting precipitate was separated by filtration, washed with water, and then vacuum-dried at 60°–80° C. for 12 hours.

The strongly alkaline mother liquor contained unreacted p-nitrophenol, mono- and diesters, and hydrolyzates thereof. In consequence, there was obtained 98.4 g of a white crystalline product melting at 154.0°–156.0° C. This product was tris(p-nitrophenyl) phosphate and its yield was 64% based on the amount of p-nitrophenol used as a starting material. It was purified by recrystallization from methanol and then subjected to elemental analysis. The results thus obtained were as follows:

|  | C(%) | H(%) | N(%) | P(%) |
|---|---|---|---|---|
| Calculated Value (for $C_{18}H_{12}O_{10}N_3P$) | 46.85 | 2.60 | 9.11 | 6.72 |
| Found Value | 46.68 | 2.66 | 8.87 | 6.75 |

EXAMPLE 2

The procedure of Example 1 was repeated except that 62.7 g (0.37 mole) of phosphorus thiochloride was used in place of the phosphorus oxychloride. In consequence, there was obtained 143.1 g (0.30 mole) of a white crystalline product melting at 171°–175° C. This product was tris(p-nitrophenyl) thiophosphate and its yield was 90% based on the amount of p-nitrophenol used as a starting material. It was purified by recrystallization from methanol and then subjected to elemental analysis. The results thus obtained were as follows:

|  | C(%) | H(%) | N(%) | P(%) | S(%) |
|---|---|---|---|---|---|
| Calculated Value (for $C_{18}H_{12}O_9N_3PS$) | 45.28 | 2.52 | 8.81 | 6.50 | 6.71 |
| Found Value | 45.01 | 2.60 | 8.59 | 6.42 | 6.63 |

EXAMPLE 3

The procedure of Example 1 was repeated except that 94.1 g (1.0 mole) of phenol was used in place of the p-nitrophenol. In consequence, there was obtained 63.0 g of a white crystalline product melting 47.5°–49° C. This product was triphenyl phosphate and its yield was 58% based on the amount of phenol used as a starting material. It was purified by recrystallization from methanol and then subjected to elemental analysis. The results thus obtained were as follows:

|  | C(%) | H(%) | P(%) |
|---|---|---|---|
| Calculated Value (for $C_{18}H_{15}O_4P$) | 66.26 | 4.60 | 9.50 |
| Found Value | 66.20 | 4.66 | 9.48 |

EXAMPLE 4

The procedure of Example 1 was repeated except that 151.2 g (1.0 mole) of N-acetyl-p-aminophenol was used in place of the p-nitrophenol and 62.7 g (0.37 mole) of phosphorus thiochloride in place of the phosphorus oxychloride. In consequence, there was obtained 157.3 g of a white crystalline product melting at 194°–196° C. This product was tris(N-acetyl-p-aminophenyl) thiophosphate and its yield was 92% based on the amount of N-acetyl-p-aminophenol used as a starting material. It was purified by recrystallization from methanol and then subjected to elemental analysis. The results thus obtained were as follows:

|  | C(%) | H(%) | P(%) | S(%) | N(%) |
|---|---|---|---|---|---|
| Calculated Value (for $C_{24}H_{24}O_6N_3PS$) | 56.14 | 4.70 | 6.03 | 6.24 | 8.18 |
| Found Value | 56.23 | 4.65 | 6.00 | 6.21 | 8.21 |

EXAMPLE 5

The procedure of Example 1 was repeated except that 32.8 g (0.30 mole) of p-aminophenol was used in place of the p-nitrophenol and the amount of phosphorus oxychloride was reduced to 16.6 g (0.108 mole). In consequence, there was obtained 22.3 g of a white crystalline product melting at 153°–155° C. This product was tris(p-aminophenyl) phosphate and its yield was 60% based on the amount of p-aminophenol used as a starting material. It was purified by recrystallization from methanol and then subjected to elemental analysis. The results thus obtained were as follows:

|  | C(%) | H(%) | N(%) | P(%) |
|---|---|---|---|---|
| Calculated Value (for $C_{18}H_{18}O_4NP$) | 58.22 | 4.89 | 11.32 | 8.36 |
| Found Value | 58.13 | 5.0 | 11.28 | 8.20 |

EXAMPLE 6

The procedure of Example 1 was repeated except that 32.8 g (0.30 mole) of p-aminophenol was used in place of the p-nitrophenol and 18.3 g (0.108 mole) of phosphorus thiochloride in place of the phosphorus oxychloride. In consequence, there was obtained 24.8 g of a white crystalline product melting at 154°–156° C. This product was tris(p-aminophenyl) thiophosphate and its yield was 64% based on the amount of p-aminophenol used as a starting material. It was purified by recrystallization from methanol and then subjected to elemental analysis. The results thus obtained were as follows:

|  | C(%) | H(%) | N(%) | P(%) | S(%) |
|---|---|---|---|---|---|
| Calculated Value (for $C_{18}H_{18}O_3N_3PS$) | 56.0 | 4.6 | 10.8 | 8.0 | 8.2 |
| Found Value | 55.6 | 4.8 | 10.7 | 8.2 | 8.1 |

EXAMPLE 7

Into a 2-liter four neck flask fitted with a stirrer, a thermometer, a condenser, and a dropping funnel was charged 900 ml of toluene. Then, 108.1 g (1.0 mole) of p-cresol was dissolved therein and 55.2 g (0.36 mole) of phosphorus oxychloride was added to the resulting solution. Immediately after that, 96.0 g (1.08 moles) of a 45%(w/w) aqueous solution of sodium hydroxide was added thereto dropwise, with vigorous stirring (at 600 rpm), through the dropping funnel over a period of about 10 minutes. During this period, cooling with water was used to keep the reaction temperature at 30° C. Thereafter, the reaction was further continued at that temperature for 5 hours.

While being kept at 30° C. or below, the reaction mixture was washed with a 30%(w/w) aqueous solution of sodium hydroxide and then with water. The resulting toluene layer was stripped of toluene and then vacuum-distilled to obtain 108 g (0.29 mole) of a colorless, transparent liquid product ($d_{20}^5$ 1.16–1.17) as the distillate boiling at 245°–260° C. under an absolute pressure of 5 mmHg. This product was tris(p-methylphenyl) phosphate and its yield was 87% based on the amount of p-cresol used as a starting material. The results of its elemental analysis were as follows:

|  | C(%) | H(%) | P(%) |
|---|---|---|---|
| Calculated Value (for $C_{21}H_{21}O_4P$) | 68.48 | 5.71 | 8.42 |
| Found Value | 68.30 | 5.79 | 8.40 |

EXAMPLE 8

The procedure of Example 7 was repeated except that 130 g (1.0 mole) of 2-ethylhexyl alcohol was used in place of the p-cresol. In consequence, there was obtained 112 g of a colorless liquid product as the distillate boiling at 210°–220° C. under an absolute pressure of 5 mmHg. This product was tris(2-ethylhexyl) phosphate and its yield was 77% based on the amount of 2-ethylhexyl alcohol used as a starting material. The results of its elemental analysis were as follows:

|  | C(%) | H(%) | P(%) | O(%) |
|---|---|---|---|---|
| Calculated Value (for $C_{24}H_{51}O_4P$) | 66.36 | 11.75 | 7.14 | 14.75 |
| Found Value | 66.33 | 11.76 | 7.11 | — |

EXAMPLE 9

Into the reaction apparatus used in Example 1 were charged 136.2 g (0.9 mole) of N-acetyl-p-aminophenol and 2,160 g of acetone. These were stirred for 30 minutes at room temperature to form a solution.

77.1 g (0.93 mole) of a 48.2%(w/w) aqueous solution of sodium hydroxide was added to the solution dropwise, with vigorous stirring (at 700 rpm), over a period of 15 minutes. During this period, external cooling was used to keep the reaction temperature at 10°–15° C. The agitation was further continued for 30 minutes. Then, 50.7 g (0.3 mole) of phosphorus thiochloride was added thereto dropwise, over a period of 1 hour. Thereafter, the reaction was further continued for 5 hours.

Acetone was removed from the reaction mixture by subjecting it to distillation at 60° C. The resulting concentrate was poured into 3,000 g of ice-water of 0°–10° C. and stirred for 30 minutes. Thereafter, the mixture was allowed to stand overnight.

The resulting precipitate was filtered, and the wet filter cake was crushed in a mortar and transferred into a 3-liter beaker. 2,000 g of ice-water and 90 g of a 45%(w/w) aqueous solution of sodium hydroxide were added thereto and the agitation was continued at 10°–20° C. for 2 hours.

The resulting precipitate was filtered and washed with water and then vacuum-dried at 80° C. for 10 hours. There was obtained 146.4 g of white crystalline tris(4-acetylaminophenonyl) thiophosphate melting at 193°–196° C. The yield was 95% based on the amount of phosphorus thiochloride.

What is claimed is:

1. In a process for the preparation of an ester compound selected from the group consisting of triaryl phosphates and triaryl thiophosphates by reaction of a phenol compound with phosphorus oxychloride or phosphorus thiochloride, the improvement which comprises reacting a phenol having on the benzene ring one or more substituents selected from the group consisting of amino, monoalkylamino, dialkylamino, monoacylamino and diacylamino groups with phosphorus oxychloride or phosphorus thiochloride in the presence of
   (a) at least one alkali metal compound selected from the group consisting of the hydroxides and carbonates of alkali metals,
   (b) water, and
   (c) an inert organic solvent, at a temperature of 80° C. or below.

2. A process as claimed in claim 1 wherein the reaction is carried out from 0° to 50° C.

3. A process as claimed in claim 1 wherein the alkali metal compound is used in the form of an aqueous solution or suspension containing the alkali metal compound at a concentration of from 20 to 60% by weight.

4. A process as claimed in claim 3 wherein the concentration of the alkali metal compound is from 30 to 50% by weight.

5. A process as claimed in claim 1 wherein the alkali metal compound is used in an amount equal to or slightly in excess of 3 moles per mole of the phosphorus oxychloride or phosphorus thiochloride.

6. A process as claimed in claim 1 wherein the phenol compound and the phosphorus oxychloride or phosphorus thiochloride are used in a molar ratio ranging from 2.5:1 to 3.5:1.

7. A process as claimed in claim 1 wherein the phosphorus oxychloride or phosphorus thiochloride is added to the phenol compound in the presence of the inert organic solvent and, while the resulting mixture is kept at a temperature of 80° C. or below, an aqueous solution or suspension of the alkali metal compound is added thereto drop by drop.

8. A process as claimed in claim 1 wherein the alkali metal compound and the water are added to the phenol compound in the presence of the inert organic solvent and, while the resulting mixture is kept at a temperature of 80° C. or below, the phosphorus oxychloride or phosphorus thiochloride is added thereto drop by drop.

9. A process as claimed in claim 1 wherein the phenol compound is an aminophenol or an N-acetylaminophenol.

10. A process as claimed in claim 1 wherein the inert organic solvent is an aliphatic ketone or an ether.

* * * * *